United States Patent
Huet et al.

(10) Patent No.: US 9,284,522 B2
(45) Date of Patent: Mar. 15, 2016

(54) PETRI DISH PROVIDED WITH MEANS FORMING EVIDENCE OF USE

(75) Inventors: Stéphane Huet, Bruz (FR); Jérôme Thepaut, Quebriac (FR); Christophe Gincheleau, Rennes (FR); Frédéric Simon, Combourg (FR); Frank Reverdy, Meillac (FR)

(73) Assignee: AEX CHEMUNEX, Combourg (FR)

( * ) Notice: Subject to any disclaimer, the term of this patent is extended or adjusted under 35 U.S.C. 154(b) by 406 days.

(21) Appl. No.: 13/806,082

(22) PCT Filed: Jun. 7, 2011

(86) PCT No.: PCT/EP2011/059366
§ 371 (c)(1),
(2), (4) Date: Dec. 20, 2012

(87) PCT Pub. No.: WO2011/160942
PCT Pub. Date: Dec. 29, 2011

(65) Prior Publication Data
US 2013/0101479 A1 Apr. 25, 2013

(30) Foreign Application Priority Data
Jun. 22, 2010 (FR) .................................... 10 54957

(51) Int. Cl.
*C12M 1/22* (2006.01)
*C12M 3/00* (2006.01)
*C12M 1/00* (2006.01)

(52) U.S. Cl.
CPC .............. *C12M 23/46* (2013.01); *C12M 23/10* (2013.01); *C12M 23/38* (2013.01)

(58) Field of Classification Search
CPC ...... C12M 23/10; C12M 23/38; C12M 23/44; C12M 23/46; B01L 3/06; B01L 3/508; B01L 2200/025; B01L 2300/041; B01L 2300/048; B65D 43/0225–43/0231; B65D 43/0277–43/0283
USPC ............. 435/288.3, 305.4; 220/290, 293–302
See application file for complete search history.

(56) References Cited

U.S. PATENT DOCUMENTS 3,158,553 A * 11/1964 Carski ........................ 435/305.4
3,704,568 A   12/1972 Duhring et al.
3,846,241 A * 11/1974 Faur et al. ....................... 435/37

(Continued)

FOREIGN PATENT DOCUMENTS

| DE | 10339083 A1 | 3/2005 |
|----|-------------|--------|
| EP | 0171174 A2  | 2/1986 |
| EP | 1035201 A1  | 9/2000 |
| GB | 886795 A    | 1/1962 |
| GB | 2106083 A   | 4/1983 |
| GB | 2117788 A   | 10/1983 |
| JP | 2003047459 A | 2/2003 |
| JP | 2003102463 A | 4/2003 |
| JP | 2003-225083 A | 8/2003 |

*Primary Examiner* — William H Beisner
(74) *Attorney, Agent, or Firm* — Harness, Dickey & Pierce, P.L.C.

(57) ABSTRACT

A Petri dish includes a receptacle and a matching lid, which both have a shape of revolution and are each delimited by a bottom wall and at least one peripheral rim. This also includes fingers and complementary locking elements. The receptacle and the lid, when rotated relative to each other, are able to occupy three or four different positions, including at least a "first position" and an "intermediate position". This dish is distinguished by the fact that the locking elements carry at least one blocking member which blocks the fingers in the "intermediate position" and which opposes the return to the "first position".

18 Claims, 12 Drawing Sheets

(56) References Cited

U.S. PATENT DOCUMENTS

| | | | |
|---|---|---|---|
| 4,084,717 A * | 4/1978 | King | 215/217 |
| 4,160,700 A | 7/1979 | Boomus et al. | |
| 4,170,861 A | 10/1979 | Snyder et al. | |
| 4,468,914 A | 9/1984 | Pestes | |
| 5,020,297 A | 6/1991 | Borie et al. | |
| 6,429,008 B1 | 8/2002 | Copeland et al. | |
| 7,105,338 B1 | 9/2006 | Holmes et al. | |
| 7,972,842 B2 | 7/2011 | Minton | |
| 2005/0089997 A1 * | 4/2005 | Minton | 435/288.3 |
| 2011/0243814 A1 | 10/2011 | Brelivet | |
| 2012/0061308 A1 | 3/2012 | Gilet et al. | |
| 2012/0125483 A1 | 5/2012 | Brelivet | |

* cited by examiner

PETRI DISH PROVIDED WITH MEANS FORMING EVIDENCE OF USE

CROSS-REFERENCE TO RELATED APPLICATIONS

This application is a National Phase Entry of International Application No. PCT/EP2011/059366, filed on Jun. 7, 2011, which claims priority to French Patent Application Serial No. 1054957, filed on Jun. 22, 2010, both of which are incorporated by reference herein.

BACKGROUND AND SUMMARY

The present invention relates to a Petri dish for cultivating micro-organisms, comprising a receptacle with a revolution shape receiving a nutritive substrate and on which rests a lid. A particularity of this Petri dish, in a specific embodiment, lies in the presence of several protrusions or fingers at the periphery of the lid, and of "attachment points" at the periphery of the receptacle receiving the protrusions of the lid.

The person skilled in the art in the field of techniques for microbiological analyses uses Petri dishes of different sizes for cultivating micro-organisms (diameters generally varying from 50 to 150 mm). The most common materials used for making these dishes are transparent plastic materials such as crystalline polystyrene (PS).

There exist two general types of Petri dishes, i.e. dishes with lugs, the receptacle of which has protrusions on which rests the lid, thereby allowing gas exchange with the inner space of the dish, and dishes without lugs not allowing gas exchange with the inner space of the dish. The person skilled in the art is aware of the benefit of managing gas exchanges for microbiological cultivation. As examples of functions fulfilled by these lugs, mention will be made of:

the gas exchange required for drying the dishes upon hot filling the receptacle of the Petri dish with nutritive substrate (gelose),
 the ventilation allowing replacement of oxygen present in the atmosphere of the internal space of the dish for cultivating anaerobic germs.

In the case of dishes without lugs, the lid rests directly on the lower receptacle, thereby limiting gas exchanges. In this case, the dryness of the nutritive substrate is lower and thus allows the nutritive substrate to be preserved for a longer time. The absence of lugs also allows an increase in the incubation time of the dish without any dryness, thereby guaranteeing better growth of "stressed" micro-organisms or with slow growth. Certain types of Petri dishes moreover allow the dish to be closed after sampling through a locking system (a lid attached by mechanical tightening or mechanical locking by rotation or clipping) so that the dish will not open by itself in order to limit risks of subsequent contaminations after sampling.

Within the scope of the present invention, the term of "sampling" has the following definition:

in the case of surface inspections, the sampling consists of applying gelose (nutritive substrate) contained in the dish on the surface to be inspected;
 in the case of air inspections, the sampling consists of opening the dish in order to collect the air to be analyzed on the gelose (either by impaction or by passive sedimentation of air on the dish);
 in the case of a microbiological inspection of a product or a micro-organism and culture, the matter will be to sow the gelose with strain or the product to be cultivated.

However, if the solutions proposed up to now allow locking of said dish in the case of a fall or tampering, it is impossible to guarantee that the dish received for cultivation has not been opened and it is therefore not possible to guarantee the security of the result and the absence of "recontamination", in fact inducing false positive results. An example of such a Petri dish is illustrated in document EP-0 171 174.

The present invention aims at solving these difficulties. In other words, its goal is to provide a Petri dish with which it is possible to ensure some traceability of the different handling operations which have been performed on the lid relatively to the receptacle (or vice versa), and most particularly when the latter have been locked beforehand. Thus, as an example, there exists an expectation for a Petri dish which, while the lid and receptacle occupy a position preventing gas exchanges, immediately informs the operator of a misguided manipulation during which this lid and this receptacle would have been separated and then brought back into the initial position.

Thus, according to the invention, we are therefore dealing with a Petri dish, which consists of a receptacle and of an additional lid, which both have a revolution shape and which are each delimited by a bottom wall and at least one peripheral wall, a wall of the receptacle or of the lid respectively bearing at least two angular equidistant fingers, generally parallel to the bottom wall, which radially protrude towards the wall of the lid or of the receptacle respectively,
 while the wall without any fingers bears a same number of locking members provided with a cam path able to receive said fingers,
 this receptacle and this lid may selectively occupy either one of the different successive positions indicated below:
  a/ a "first position", a so-called "non-locked beforehand" position, in which said fingers are not received into said locking members;
  b/ at least one "intermediate position" selected from:
   a "non-ventilated locked" position, in which said fingers are received in said locking members and in which the receptacle is in intimate contact with the lid, so that the internal space which they delimit is isolated from the outside medium, and
   a "locked and ventilated" position in which said fingers are received in said locking members and in which the receptacle is not in intimate contact with the lid, so that the internal space which they delimit is not isolated from the outside medium;
  c/ a "final position", a so-called "read out" position, in which said fingers are released from said locking members and allow the lifting of said lid,
 the passing from one position to the next position being accomplished at least by relative rotation of the lid relatively to the receptacle, in a same direction.

This dish is remarkable in that said locking members bear at least one means for blocking the fingers in the "intermediate position", which opposes return to the "first position" while allowing passing to the next position. By the presence of this blocking means, it is normally not possible to bring the receptacle and lid back into the preceding position. This "locking" ensures the operator of the "status" of the dish being in the "intermediate position".

Moreover, according to other advantageous and non-limiting characteristics:

said blocking means is an anti-return ratchet;
 said fingers have a region forming an interior angle, capable of forming an abutment for the ratchet;
 said anti-return ratchet is retractable;

said cam path is delimited by the wall itself and by a "lug" of material secured to the wall, this wall and this "lug" delimiting transversely, i.e. along a direction generally perpendicular to the direction of the relative displacement of a finger, a corridor for entering said finger and guiding it along the cam path between the "first position" and the "final position";

it includes indicating means positioned at the entry of said corridor, and/or at its exit, the initial condition of which is modified upon passing from the "first position" to the "intermediate position", from the "intermediate position" to the "final position", respectively, this change of state being visually perceptible;

said indicating means comprise at least one tab secured to the wall and to the lug which, in the modified state, is detached from one of said wall and lug;

in the modified state, said tab is secured to said lug and is immobilized in the raised position;

said lug is retractable outwards, i.e. in a direction generally opposite to the lid;

said other wall bears a protrusion which, upon passing from the "intermediate position" to the "final position", exerts a force on said lug and retracts it.

Other features and advantages of the invention will become apparent upon reading the following detailed description of preferred embodiments.

BRIEF DESCRIPTION OF THE DRAWINGS

This description will be made with reference to the appended drawings wherein:

FIGS. 9 to 11 are detailed views of the lid and of the receptacle, in different relative positions, in which a locking finger occupies positions which will be detailed later on;

DETAILED DESCRIPTION

Figure 1:
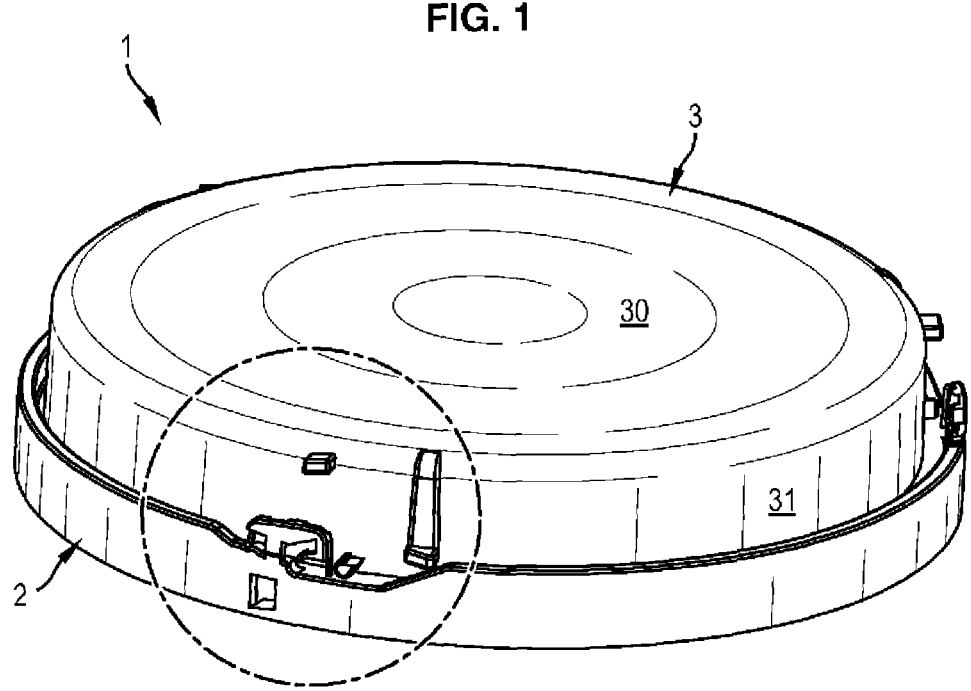
FIG. 1 is a perspective view of a first embodiment of a Petri dish according to the invention.

Reference will now be made to FIGS. 1 to 15 for giving details of the structure of the first embodiment of the Petri dish according to the invention. As this is more particularly visible in FIGS. 1, 3 and 5, the Petri dish 1 consists of a receptacle 2 and of a lid 3, for example both in a transparent plastic material such as crystalline polystyrene. The receptacle 2 has a revolution shape and includes a bottom 20 with a circular contour, the upper surface of which is planar and the periphery of which is vertically delimited by a first wall 22, a so-called "inner wall". As this is particularly visible in FIG. 3, this wall 22 has on its external face, small overthicknesses 220 which have the shape of small pillars and the function of which will be explained later on.

The bottom 20 continues radially beyond the first wall, in order to form a peripheral path 23, itself delimited by said wall 22, as well as a second wall 21, a so-called "outer wall", with a generally cylindrical shape. This outer wall 21 has dimensions such that its top, materialized by the planar surface referenced as 210, parallel to the bottom 20, is located at a lower level at the top of the first wall 22. On the other hand, this outer wall 21 continues beyond the bottom 20. In other words, it continues downwards beyond the bottom 20 and the peripheral path 23. This may notably be seen upon examining FIGS. 2 and 4, it is seen that the outer wall 21 has in localized regions, notches 211 in which its rated height is considerably reduced.

Figure 2:
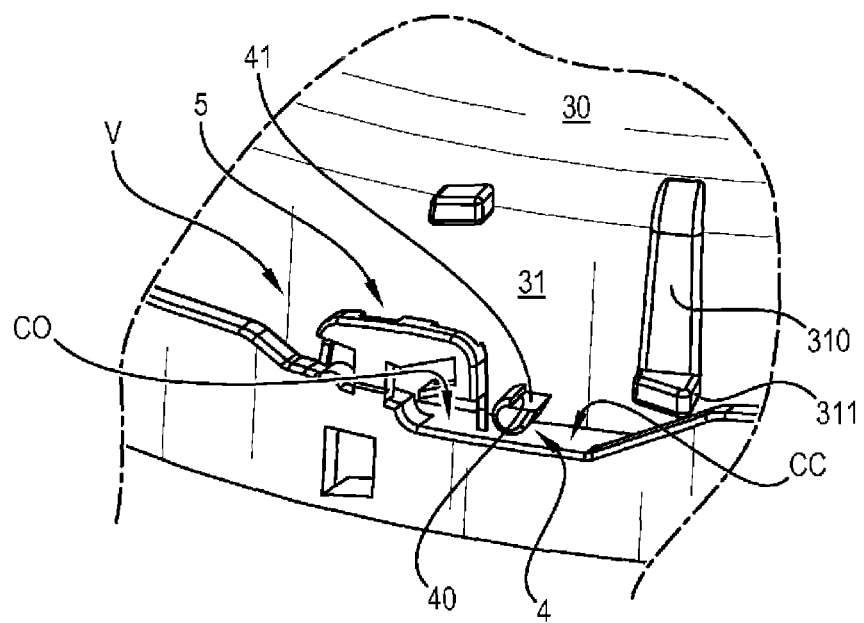
FIGS. 2, 4 and 6 are enlarged views of the region surrounded by a circle, as visible in FIGS. 1, 3 and 5.
Figure 3:
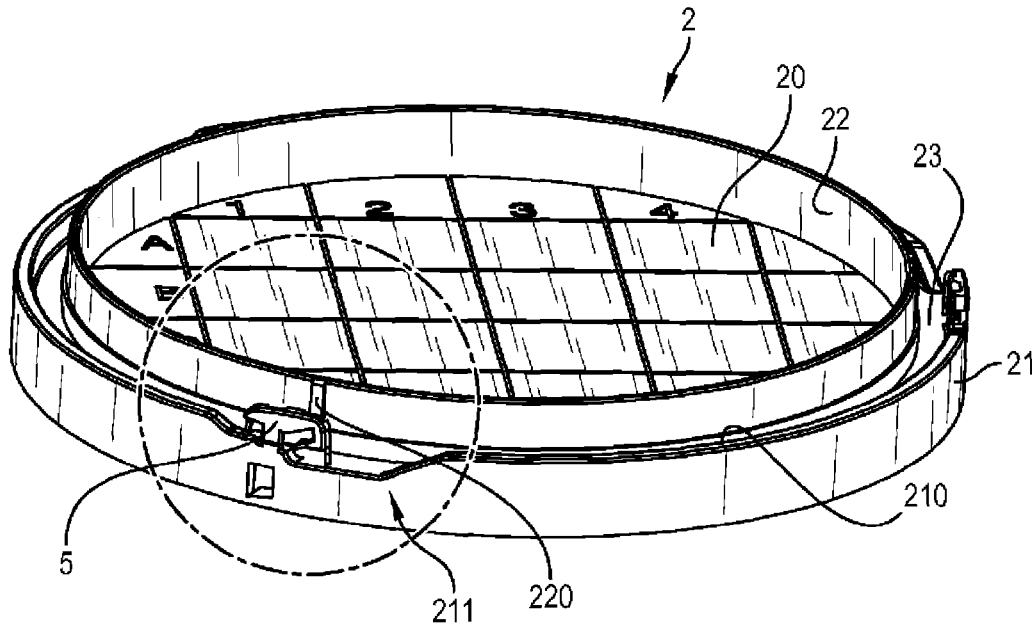
FIG. 3 is a perspective view of the receptacle of the Petri dish of FIG. 1, without its lid.
Figure 4:
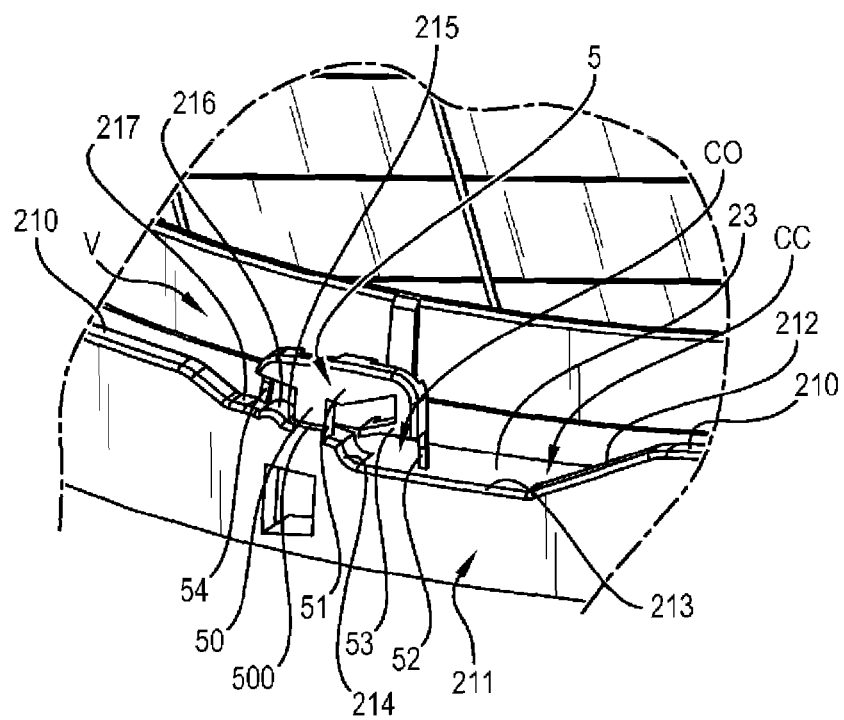

In this case, in the illustrated embodiment, these notches are three in number and are angularly equidistant from each other. They are found placed, facing overthicknesses forming pillars 220. These notches 211, when FIGS. 2 and 4 are considered, are formed from right to left of these figures, with a rectilinear segment 212 with a downward slope, with a horizontal and planar segment 213, which is at the same level as the aforementioned path 23. This notch continues with a curved area 214 with an upwards slope, which continues through two successive convex regions 216, which surround a recess 215.

Finally, two areas 217 and 218 with an upwards slope are connected to the top 210 of the wall 21, at the same level as initially. All these segments and areas 212 to 218 form a cam path CC.

In these notched regions, and particularly between the areas 214 and 215, a "lug" 5 rises vertically, made by molding with the receptacle 2, which is connected to the wall 21 through a pillar 50. In this embodiment, the pillar has the particularity of including a mechanically weakened area 500, for example as a groove which runs transversely through its base. The body 51 of the lug 5 is connected to this pillar along a direction which is generally that of said wall. The cam path CC and the lug 5 delimit a corridor CO and form a locking member V.

This body 51, in its "upstream" portion, turned towards the right of FIG. 4 is extended with a tab 52 which is secured to said body 51 but also to the receptacle 2. This tab, as this will be explained later on, has the particularity of being able to have a modified (state) condition in which it is either detached from the wall 21, or from the lug 5. Preferably, in this modified condition, the tab 52 is secured to the lug 5 and is immobilized in the raised position.

The body 51 moreover includes an anti-return ratchet 53 which is oriented obliquely downwards, towards the aforementioned area 214 which has a curved upward slope. There again, we shall refer back to the structure and to the operation of this anti-return ratchet, later on in the description. The so-called "downstream" opposite end of the body 51 also includes a tab 54 which has the same characteristics as those referenced as 52 and already described.

Figure 5:
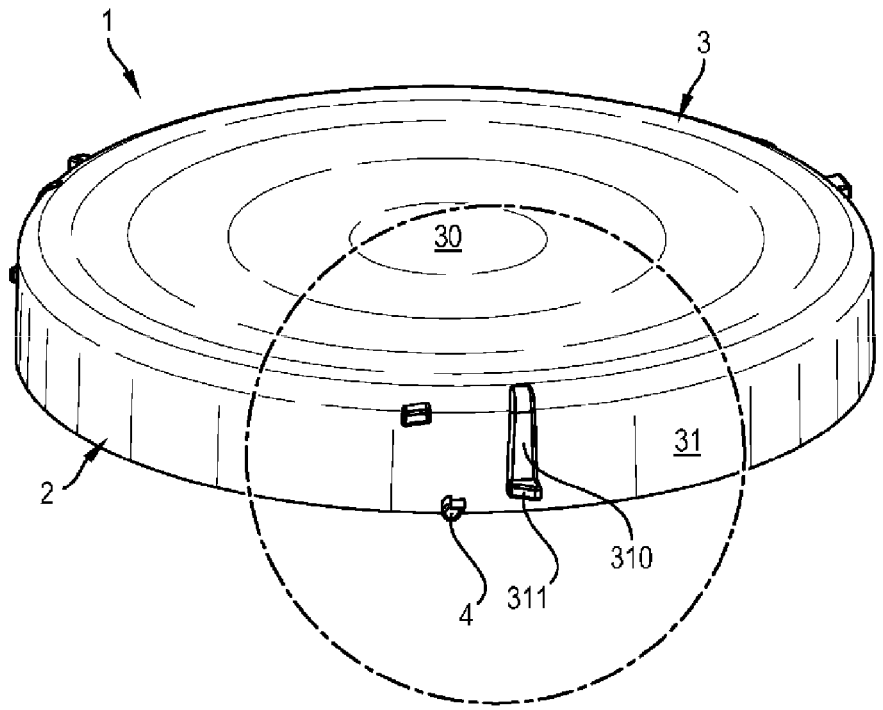
FIG. 5 is a perspective view of said lid alone.
Figure 6:
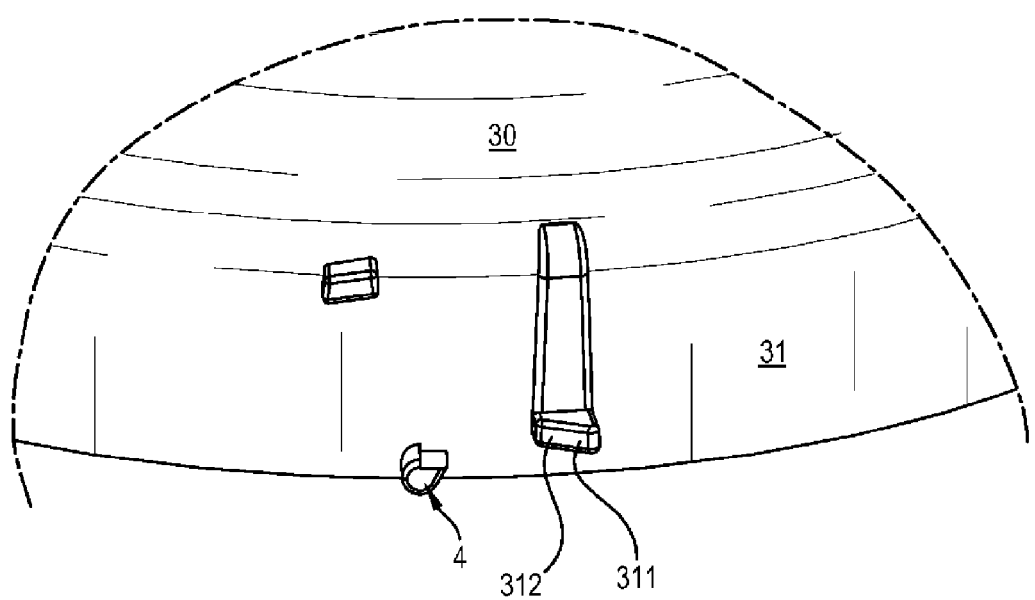
Figure 7:
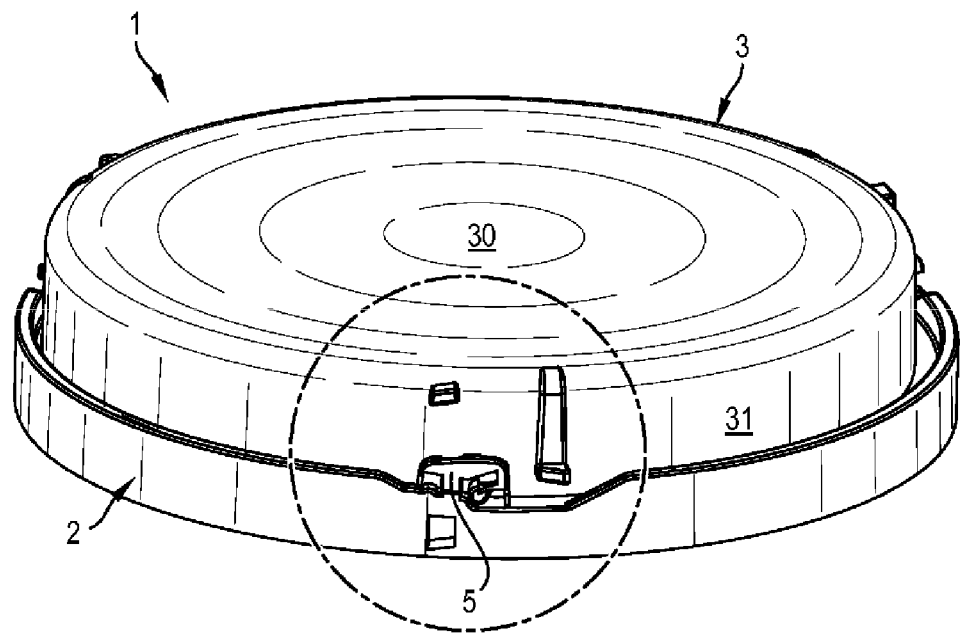
FIG. 7 is a similar view to FIG. 1 showing a particular positioning of the lid and receptacle relatively to each other, in this case in a so-called "intermediate", non-ventilated locked position.
Figure 8:
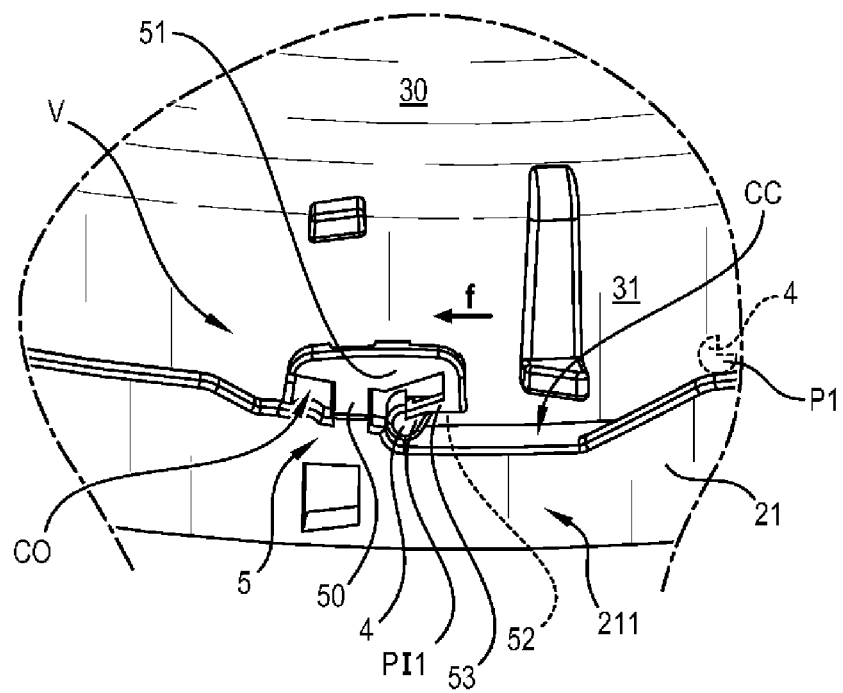
FIG. 8 is an enlargement of the area marked by a circle in FIG. 7.

Now referring notably to FIG. 5, it is seen that the lid 3 bears, on the external face of its peripheral wall 31, equidistant fingers referenced as 4, and three in number in the illustrated embodiment. These fingers 4 protrude radially outwards and extend in a horizontal position. They are located just below the wall 31, along its lower edge. As this is more particularly visible in FIGS. 2 and 4, these fingers have a substantially ovoidal cross-section, with an interior angle 40, the function of which will be explained further on. In a different embodiment, the cross-section may be circular.

This interior angle 40 is located at a cut-out 41 provided in the right upper quarter of the finger 4. Not far from each finger extends a substantially vertical pillar 310 which forms a whole with the wall 31 and forms an overthickness thereof.

At the base of this overthickness, a protrusion 311 having a cut face referenced as 312, extends radially outwards. As shown more particularly in FIGS. 5 and 6, the protrusion 311 is located at a level slightly above that of the neighbouring finger 4 and is positioned on the right of the latter when said figures are considered. The respective heights of the walls 22 of the receptacle and those 31 of the lid are such that this lid 3 may rest through the lower edge of the wall 31, against the bottom 23 of the receptacle, between the walls 21 and 22. This is the position illustrated in FIG. 1.

We shall now explain how such a Petri dish is used. In this case, we shall successively describe four positions which the receptacle and the lid are able to occupy relatively to each other and we shall also refer back to the way how the pieces of equipment described earlier co-operate with each other. Even before such a Petri dish is used and receives gelose or a nutritive substrate, a user receives said dish in a position called a first position and said to be "non-locked beforehand".

In this position, the lid is positioned on the receptacle 2 so that the three fingers 4 rest on the wall 21. This position is marked by an outline in dashed lines in FIG. 8 and is designated as P1. In such a position, the fingers 4 are "free to move" and the lid 3 is only retained on the receptacle 2 by the fact that the internal face of its wall 31 causes slight friction on the pillars 220, with which the internal wall 22 is provided.

Once after having proceeded with the removal of the lid, and with the sampling operations, the lid 3 is repositioned and rotation over a fraction of a turn is imparted to it so that the fingers initially bearing upon the top of the wall 21 move down the slope 212 of the notches 211 and will rest on the area 213. By continuing this movement in the same direction (arrow f, FIG. 8), the fingers are engaged into the locking means integrated to the lug 5. More specifically, and with reference to FIGS. 2, 9 and 10, said rotary movement is imparted to the lid until each of the fingers 4 is positioned facing the corresponding lug 5, just in front of the tab 52, (position of FIG. 2).

Figure 9:
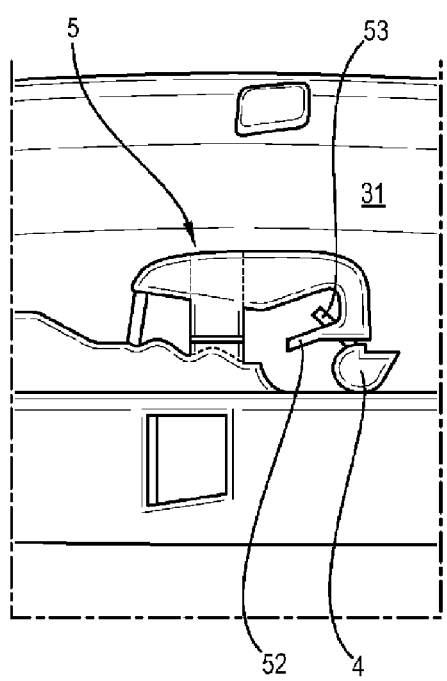
Figure 10:
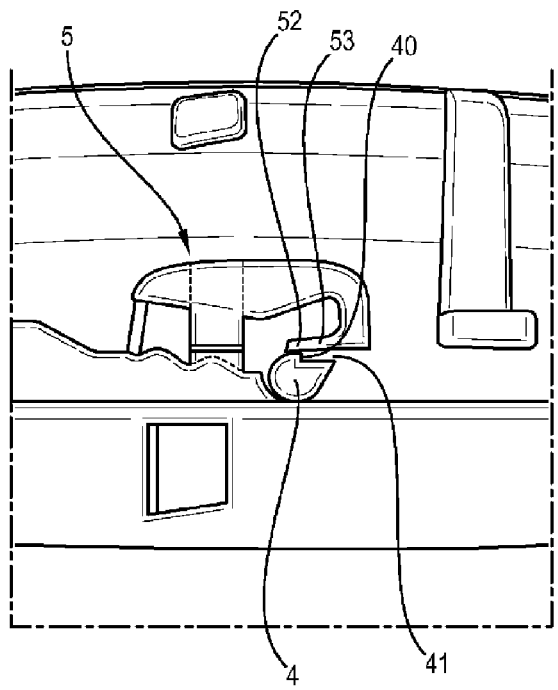

By continuing the movement, this indicator formed by the tab 52, is pushed and is detached from the wall 31 so as to be raised, as shown in FIG. 9. This change in the state of the tab 52, therefore gives the possibility of visually accounting for the fact that the lids 3 and receptacle 2 are no longer in the so-called "non-locked beforehand" "first position" but in an "intermediate position".

According to the invention, the members V for locking the Petri dish include a means for blocking the fingers 4 in the intermediate position, which oppose the return to the "first position", while allowing passing to the next position. In this case, and with reference to FIG. 10, when the movement is continued in the same direction, the top of the finger 4 raises the anti-return ratchet 53 until the finger moves beyond it and said ratchet will be housed in the interior angle 40. It is now found in the "non-ventilated locked", "intermediate position" referenced as PI1 in FIG. 8.

In this locked position, the wall 31 is in contact with the bottom of the receptacle 2 (peripheral path 23), so that the internal space of the Petri dish is isolated from the outside medium. In this intermediate position, the anti-return ratchet 53 is opposed to the movement of the finger 4 in a direction opposite to the one which was given to it initially. Thus, one is therefore sure, always in a way visible from the outside, that the position of the Petri dish is locked.

If, inadvertently, an operator attempted to bring the lid 3 and the receptacle 2 back into the preliminary position PI, he/she would then be forced to act against the anti-return ratchet, by retracting it. By the term of "retracted", is meant that the ratchet may be brought into a position in which it no longer opposes the movement of the finger 4, in particular, by being raised, thanks to a mechanically weakened area forming a joint. However, if such a manipulation was carried out, the raised positioning of the ratchet then immediately gives information on the manipulation which was carried out.

Figure 11:
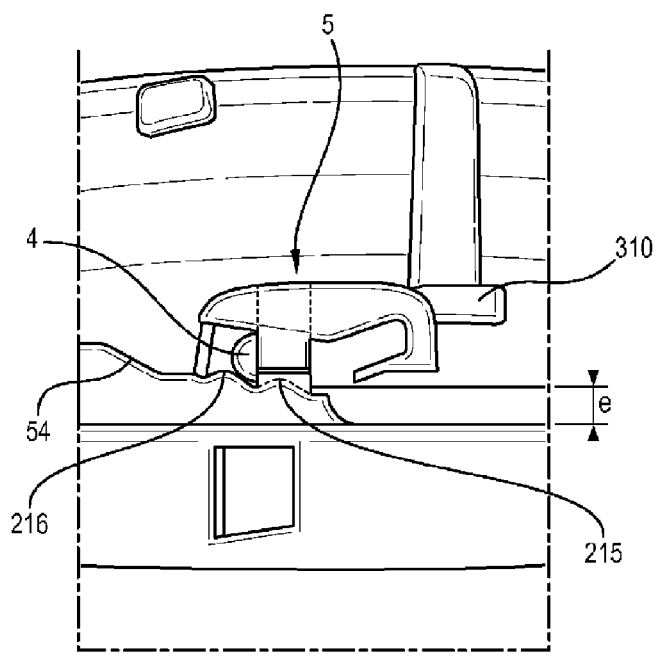
Figure 12:
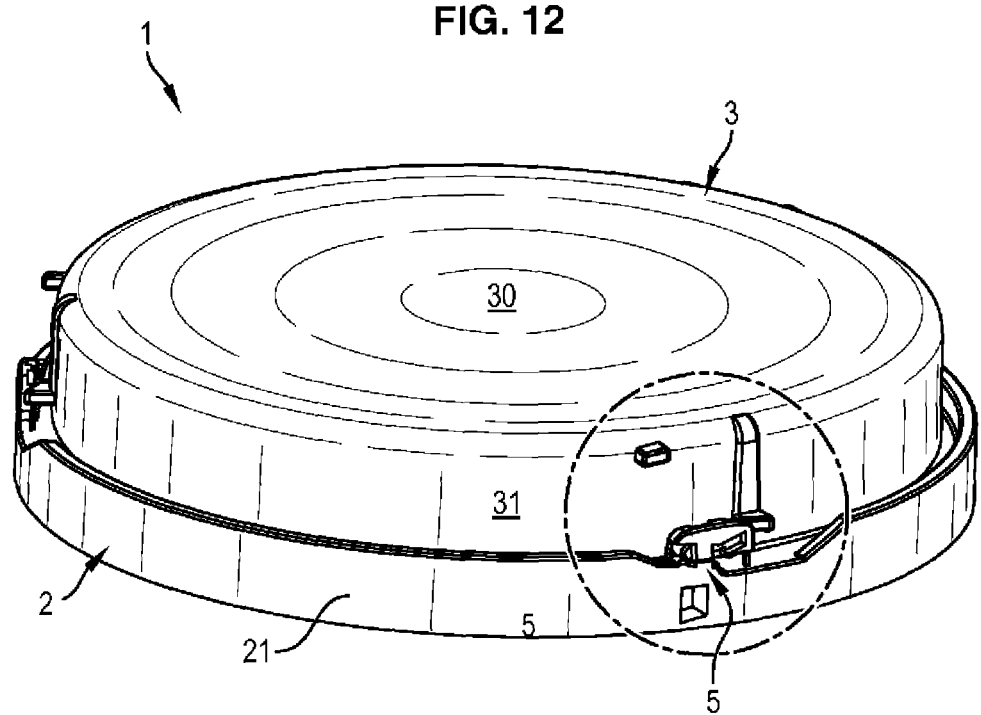
FIGS. 12 and 13 are views of the Petri dish in the position partly illustrated in FIG. 11.
Figure 13:
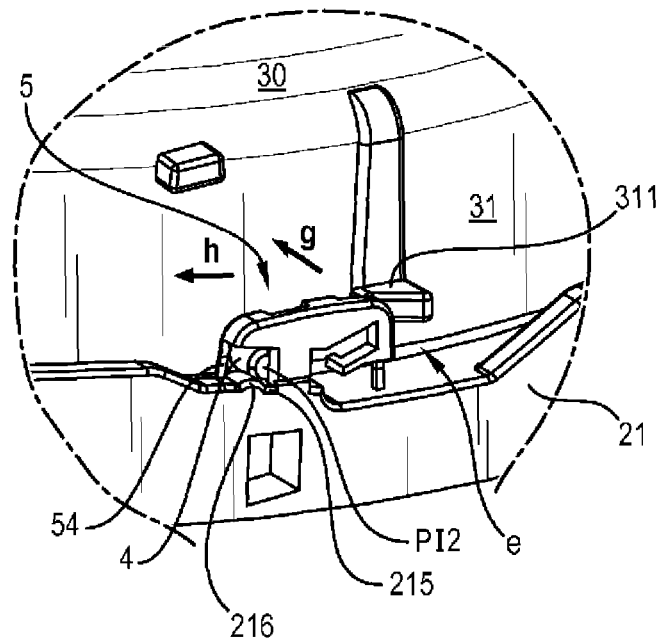

In the case illustrated here and although this is not mandatory, it is possible to further display the finger 4 for having it occupy another intermediate so-called "locked and ventilated" position in which the fingers 4 are always received in the locking members V but wherein the receptacle 2 is no longer in intimate contact with the lid 3, so that the internal space which they delimit is no longer isolated from the outside medium. This position is illustrated in FIGS. 11 and 13 and is obtained by always displacing the lid in the same direction and by additionally imparting to it a translational upward movement (arrows g and h). With this movement the fingers may move beyond the ramp 214 so that they come to a stable position materialized by the area 215 surrounded by both convex portions 216.

Although this is not illustrated in this embodiment, it is quite possible to envision that the lug 5 bears in this region a ratchet similar to the ratchet 53 already described, so as to form a means for blocking the fingers in this intermediate position PI2, while opposing the return to the first position PI1. In this intermediate position PI2, the lid is raised by a height e, corresponding to the level difference between the area 215 and the area 213, this space e being put to work for ventilating the inside of the Petri dish.

When the cultivation is finished and an operator wishes to proceed with removal of the lid in order to have direct access to the inside of the receptacle, he/she causes the receptacle 2 of the lid 3 to occupy a last final so-called "read out" position, in which the fingers 4 are released from the locking members V and allow lifting of the lid 3. This is again accomplished by a rotary and relative movement of the lid 3 relatively to the bottom 2, always in the same direction. By doing this, each finger 4 will force against the second tab 54, the initial state of which is modified and which retracts while remaining secured, in the raised position, to the lug 5. Again, the passing from one position to the other is visible and may be identified.

Figure 14:
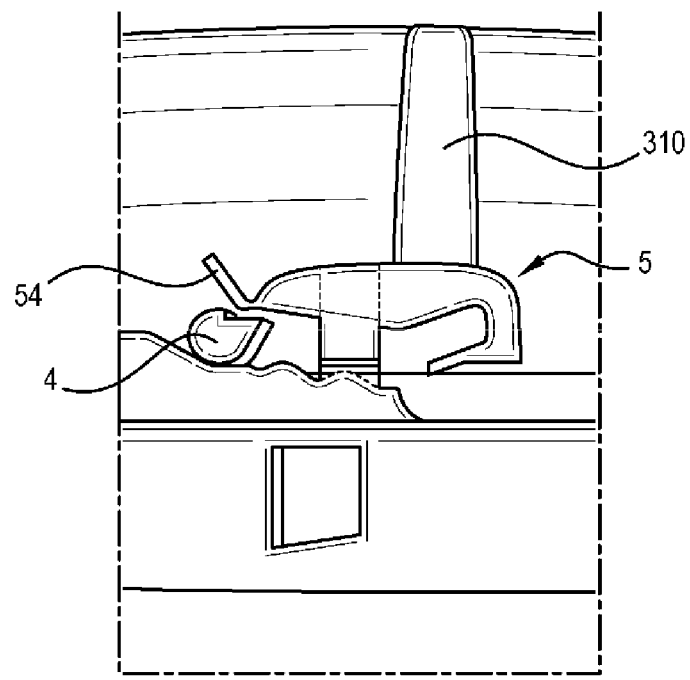
FIG. 14 is a detailed view of the relative positioning of the lid and of the receptacle, in a final so-called "read out" position.
Figure 15:
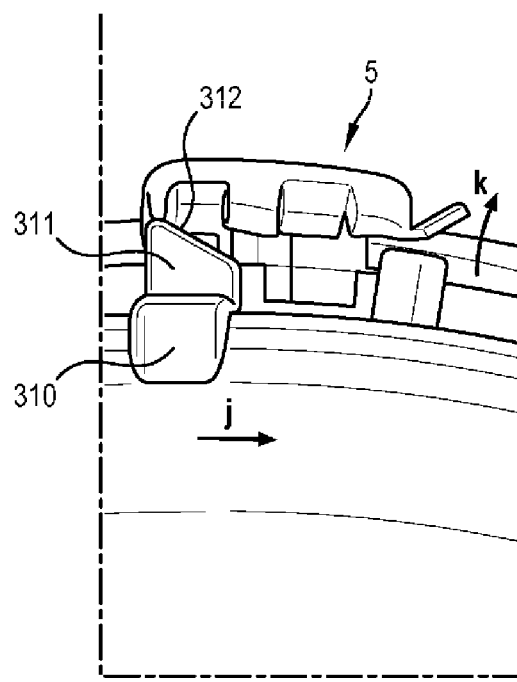
FIG. 15 is a top view corresponding to the position of FIG. 14.
Figure 16:
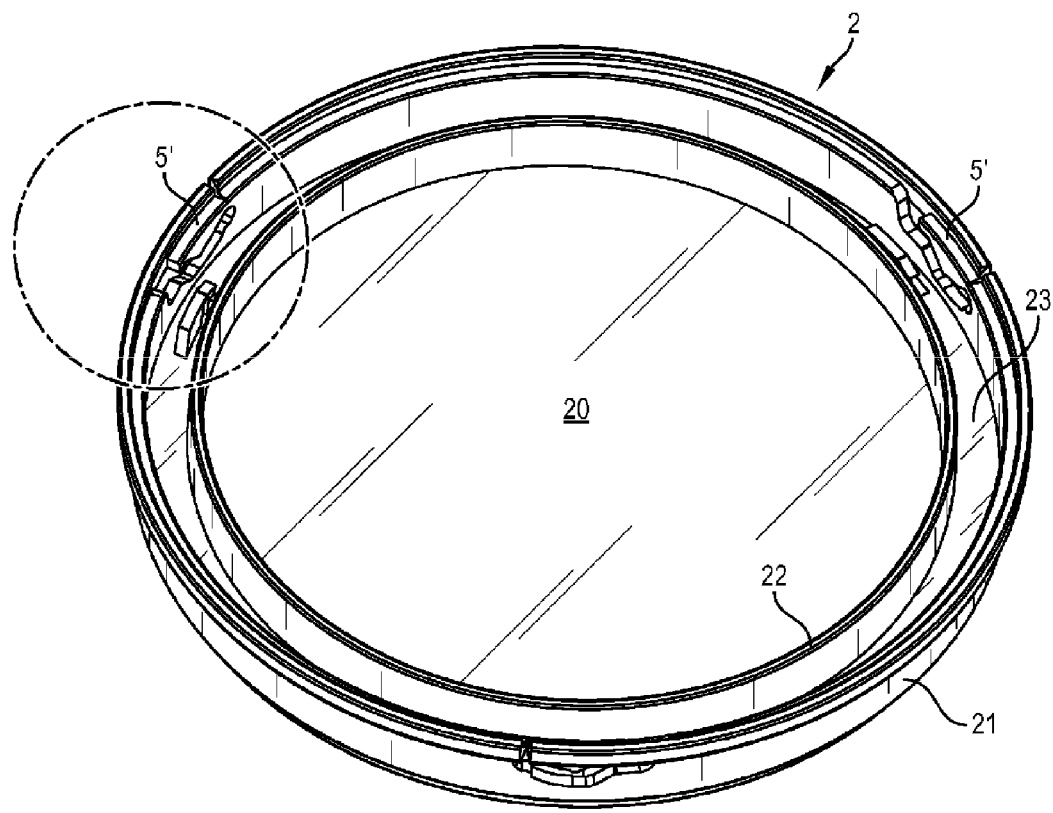
FIG. 16 is a perspective view of a receptacle according to another embodiment of the invention.
Figure 17:
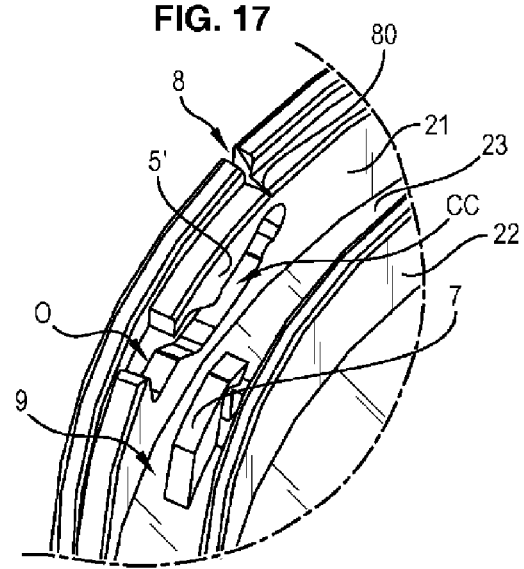
FIG. 17 is an enlarged view of the area located by a circle in the preceding view.

During this operation and as shown more particularly by the comparison of FIGS. 11, 14 and 15, the protrusion 311 borne by each of the pillars 310 will interfere with the corresponding lug 5, which, because of the low resistance area 500, bends and retracts outwards. Thus, this retracted position is the unquestionable indication of the passing from the preceding intermediate position to the final position. If this position was inadvertently obtained with a manipulation error, then the action of the lug 5 would immediately give information on the status of the dish, which would automatically allow it to be discarded since it is not compliant with the requirements in this matter.

As indicated above, in this embodiment, two intermediate so-called "ventilated" and "non-ventilated" positions are provided. However, it is possible to envision Petri dishes which would only allow one of these intermediate positions to be obtained.

Figure 4A:
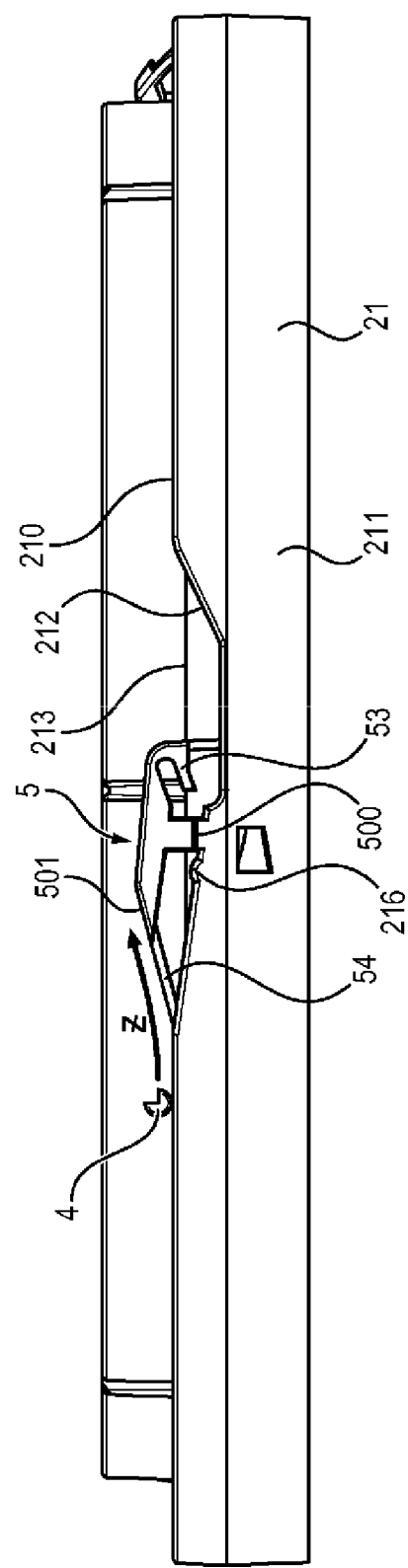
FIG. 4A is a front view of a receptacle provided with an alternative embodiment of locking means.

The receptacle of FIG. 4A substantially shows the same structure as that of the figures described earlier. However, the "lug" 5 is essentially different from that of the preceding embodiment by the shape of the upper face of the latter, which has an angled shape, with an end portion 501 which is oriented obliquely towards the edge of the wall 21. Moreover, the second tab 54 extends in the continuity of the end portion 501. In this way, more resistance to the forces is given to this tab, so that it only retracts when it is voluntarily urged.

Moreover, at the moment when the lid of the Petri dish is positioned on the receptacle, the finger 4 may be positioned not upstream from the lug 5, but downstream therefrom. In this case, by performing a rotation in the anticlockwise direction of the lid relatively to the receptacle, as shown by the arrow Z, the finger 4 is displaced along the tab 4, which acts as a springboard.

In FIGS. 16 to 23, a second embodiment of the Petri dish is described. The latter is very close to the embodiment already described, notably as regards the structure of the receptacle 2. In this case, the bottom wall 20 is connected to two outer 21 and inner 22 cylindrical walls, separated by a ring-shaped peripheral path 23.

In three angularly equidistant areas, the outer wall 21, bears as cut-outs made in the thickness of the wall, three cam paths CC accessible through the top of the wall, via an opening O. As this is visible in FIG. 17, notably, the cam path CC is delimited upwards by a lug 5' which is made with the wall 21 in the same material. Opposite to the aforementioned opening O, this lug 5' has a partial cut-out 8 and only holds on to the remainder of the wall through a small material strip referenced as 80. As this is further shown by this figure, this receptacle includes a blocking means as an anti-return ratchet 7, which is not integrated within the lug 5' like in the first embodiment, but extends at the path 23 separating both aforementioned walls. The ratchet is separated from the outer wall by a passage 9 with a curved profile, the function of which will be explained.

Figure 18:
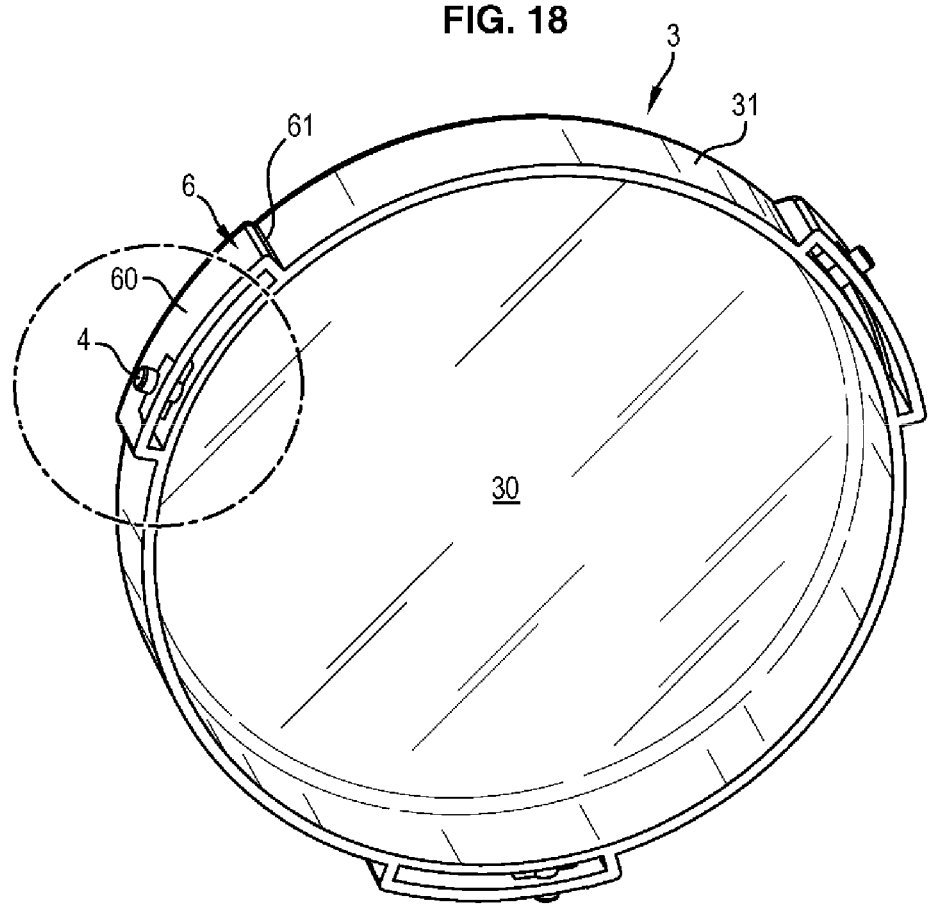
FIG. 18 is a perspective view from below of the lid of the second embodiment.
Figure 19:
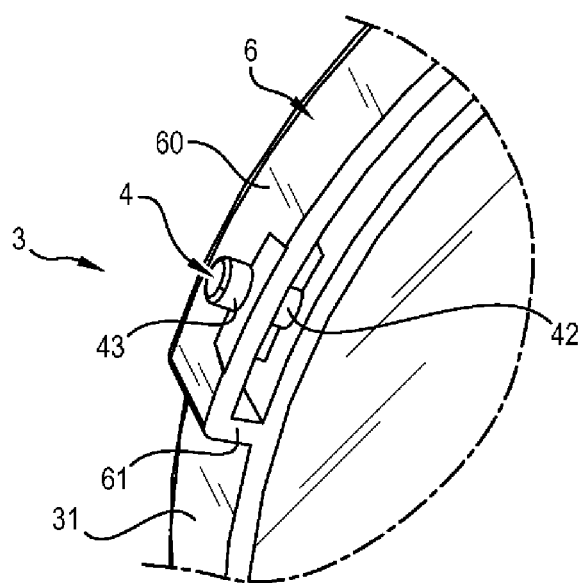
FIG. 19 is an enlarged view of the area marked by a circle in the preceding view.
Figure 20:
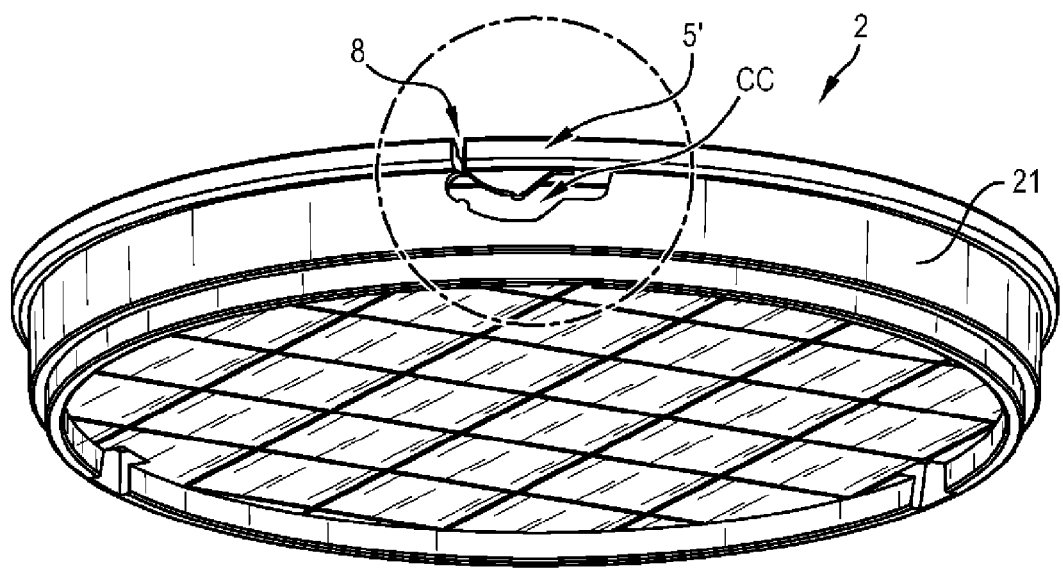
FIG. 20 is a perspective view of the receptacle of FIG. 16, according to another viewing angle.
Figure 21:
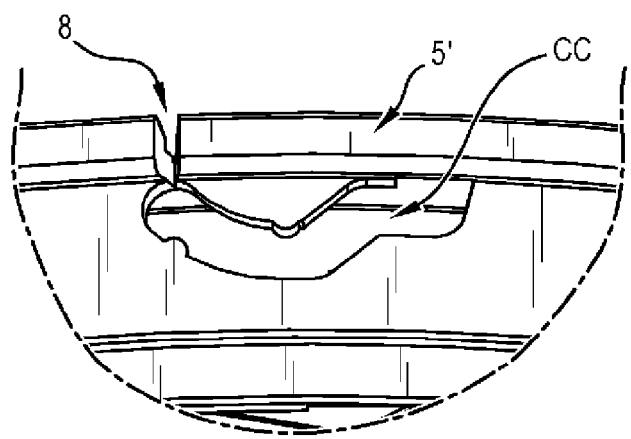
FIG. 21 is a larger view of the area marked by a circle in the preceding figure.
Figure 22:
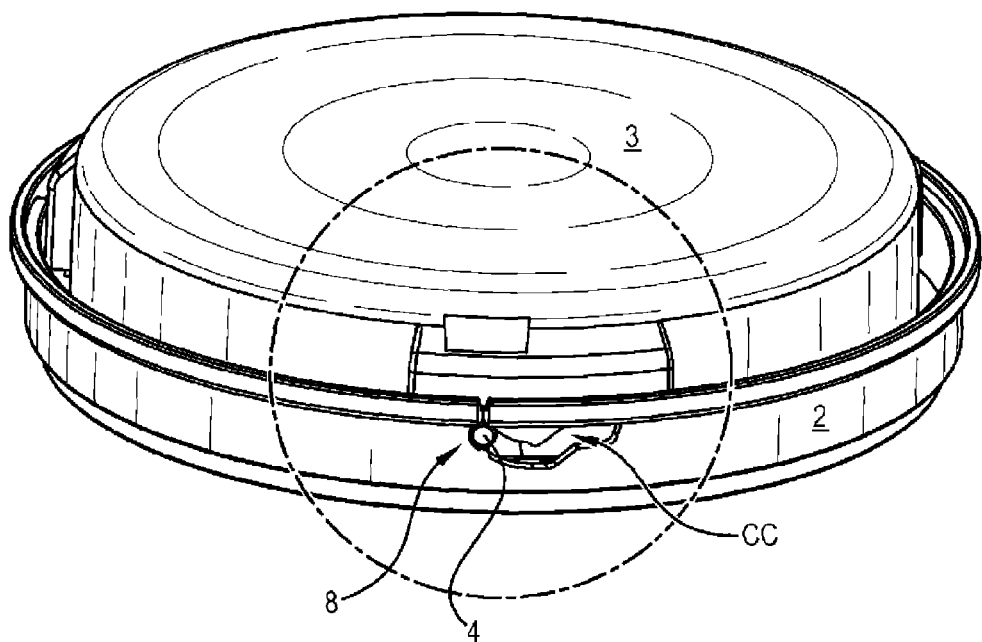
FIG. 22 is a perspective view of the assembled lid and receptacle, in a particular position corresponding to a locked and ventilated position.
Figure 23:
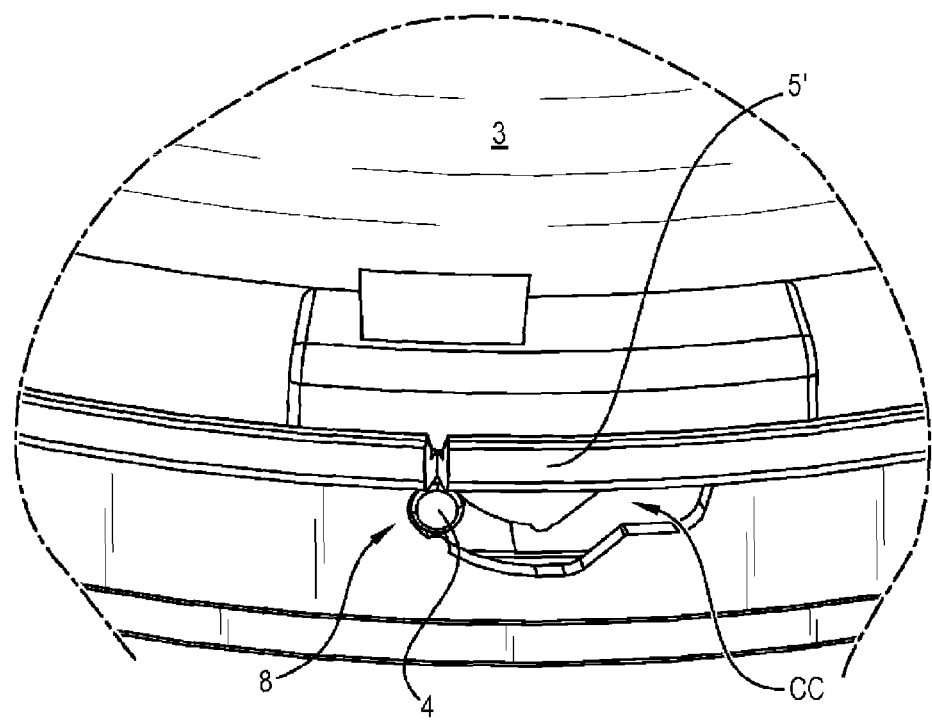
FIG. 23 is an enlarged view of the area marked by a circle in the preceding figure.

In FIGS. 18 and 19, a lid 3 is visible which is intended to cooperate with the receptacle which has just been described. Like in the previous embodiment, this lid includes a bottom wall 30 and a peripheral wall 31. In three angularly equidistant regions, the external barrier of the wall 31 bears an additional partition 6, the body 60 of which is located at a constant distance from the wall 31, and which is connected to the latter through two opposite tabs 61. The curvature and the thickness of the body 60 substantially, within the play, correspond to the dimensions of the space forming a corridor 9 which has been described with reference to FIG. 17.

From the wall 31 through the additional partition 6, extend fingers 4, the portion located between the wall strictly speaking and the partition 6 being referenced as 42, while the end forming an outer protrusion is referenced as 43. The dimensions of the fingers 4 are provided so that they may be engaged, when they are positioned for this purpose, into the opening O of the aforementioned cam path. By doing this, and as soon as the lid will have been displaced relatively to the receptacle, the ratchet 7 will oppose the return of the receptacle 2 and of the lid 3 into the preceding position, i.e. said "first position". However, if a significant effort is made in this direction, then the ratchet is provided for being retracted, or even being broken. By this characteristic, one then has a visible indicator of the manipulation of the dish.

The lid relatively to the receptacle is caused to occupy the whole of the desired positions, it is then sought to have them occupy the final position already described in which the fingers 4 are no longer locked and allow lifting of the lid 3. This is made possible by lifting the lid when the fingers are found at the end of the cam path CC, just facing the aforementioned cut-out (partial cut-out 8). Because of the low mechanical strength of this area, it is possible to at least partly detach the lug 5' from the wall 21, allowing release of the fingers 4. One then has the visual information according to which the Petri, dish has occupied at a given moment, the final so-called "read out" position. Under these conditions, even if the fingers are again engaged onto the cam path CC, the modification of condition of the lug 5' would be visible and would show that a preliminary manipulation has been applied.

The invention claimed is:

1. A Petri dish comprising:
   a receptacle and of an additional lid, which both have a revolution shape and which are each delimited by a bottom wall and at least one peripheral wall;
   a wall of said receptacle or respectively of said lid bearing at least two angularly equidistant fingers generally parallel to said bottom wall, which radially protrude towards said wall of said lid or respectively of said receptacle;
   while said wall without any fingers bears a same number of locks provided with a cam path able to receive said fingers;
   this receptacle and this lid may selectively occupy either one of successive different positions indicated below:
   (a) a first position, a so-called "non-locked beforehand" position, in which said fingers are not received in said locks;
   (b) at least one "intermediate position" selected from:
      (i) a "non-ventilated locked" position, in which said fingers are received in said locks in which said receptacle is in intimate contact with said lid, so that an internal space which they delimit is isolated from an outside medium, and
      (ii) a "locked and ventilated" position in which said fingers are received in said locks and in which the receptacle is not in intimate contact with said lid, so that said internal space which they delimit is not isolated from said outside medium;
   (c) a "final position", a so-called "read out" position, in which said fingers are released from said locks and allow lifting of said lid;
   passing from one position to a next position being accomplished at least by a relative rotation of relatively to said receptacle, in a same direction;
   wherein said locks bear at least one blocking member which blocks said fingers in an "intermediate position", which opposes the return to the "first position", while allowing passing to said next position, said blocking member being an anti-return ratchet.

2. The dish according to claim 1, wherein said fingers have a region forming an interior angle, capable of forming an abutment for the ratchet.

3. The dish according to claim 1, wherein said anti-return ratchet is retractable.

4. The dish according to claim 1, wherein said cam path is delimited by the wall itself and by a "lug" of material secured to said wall, this wall and this "lug" delimiting transversely along a direction generally perpendicular to the relative displacement direction of said finger, a corridor for entering said finger and guiding it along a cam path between said "first position" and said "final position".

5. The dish according to claim 4, further comprising an indicator positioned at the entry of said corridor and/or at its exit, the initial condition of which is modified upon passing from said "first position" to said intermediate position", from said "intermediate position" to said "final position", respectively, this change of state being visually perceptible.

6. The dish according to claim 5, wherein said indicator comprises at least one tab secured to said wall and to said lug, which, in the modified state is attached from one of said wall and said lug.

7. The dish according to claim 6, wherein in the modified state, said tab is secured to said lug and is immobilized in a raised position.

8. The dish according to claim 4, wherein said lug is retractable outwards in a direction generally opposite to said lid.

9. The dish according to claim 8, wherein said other wall bears a protrusion which, during the passing from said "intermediate position" to said "final position", exerts a force on said lug and retracts it.

10. A Petri dish comprising:
a receptacle having a bottom wall and a peripheral wall;
a lid having a bottom wall and a peripheral wall; and
a ratchet mechanism that allows rotation of said lid relative to said receptacle in a first direction and prevents rotation of said lid relative to said receptacle in a second direction that is different than the first direction;
wherein said ratchet mechanism includes a finger and a ratchet, said finger extending from said peripheral wall of said lid, said ratchet being connected to said peripheral wall of said receptacle; and
wherein, as said lid is rotated in said first direction, said finger moves along a cam path defined by at least one of said bottom wall of said receptacle and said peripheral wall of said receptacle.

11. The dish according to claim 10, wherein said lid is rotatable in said first direction from a first position, in which said lid is removable from said receptacle without rotating said lid, to a second position, in which said lid is not removable from said receptacle without rotating said lid.

12. The dish according to claim 11, further comprising a lug that is connected to said peripheral wall of said receptacle and that includes said ratchet, wherein said lug is disposed over said finger when said lid is in said second position to prevent said lid from being raised from said receptacle.

13. The dish according to claim 11 wherein, when said lid is rotated from said first position to said second position, said finger moves said ratchet out of a travel path of said finger until said finger is moved past said ratchet.

14. The dish according to claim 13 wherein, if said lid is rotated in said second direction when said lid is in said second position, said ratchet engages said finger to prevent said lid from rotating from said second position to said first position.

15. The dish according to claim 11 wherein, when said lid is in said second position, said peripheral wall of said lid contacts said bottom wall of said receptacle such that an internal space of said Petri dish is sealed.

16. The dish according to claim 15 wherein said lid is rotatable in said first direction from said second position to a third position in which said lid is not removable from said receptacle without rotating said lid and said peripheral wall of said lid does not contact said bottom wall of said receptacle such that said internal space of said Petri dish is not sealed.

17. The dish according to claim 16 wherein said lid is rotatable in said first direction from said third position to a fourth position in which said lid is removable from said receptacle without rotating said lid.

18. The dish according to claim 17 wherein said cam path is defined by said peripheral wall of said receptacle, and said cam path includes a plurality of segments corresponding to said first, second, third, and fourth positions.

* * * * *

UNITED STATES PATENT AND TRADEMARK OFFICE
CERTIFICATE OF CORRECTION

PATENT NO. : 9,284,522 B2
APPLICATION NO. : 13/806082
DATED : March 15, 2016
INVENTOR(S) : Stéphane Huet et al.

Page 1 of 1

It is certified that error appears in the above-identified patent and that said Letters Patent is hereby corrected as shown below:

Title Page 1, Column 1, Assignee, delete "AEX CHEMUNEX" and insert -- AES CHEMUNEX --.

Signed and Sealed this
Fifth Day of July, 2016

Michelle K. Lee
*Director of the United States Patent and Trademark Office*